United States Patent [19]

Dehming

[11] Patent Number: 4,613,419
[45] Date of Patent: Sep. 23, 1986

[54] NOVEL GEL ELECTROPHORESIS CELL HAVING A LOWER BUFFER CHAMBER WITH PERFORATED SHOULDER FOR HOLDING GEL TUBES OR CHANNELS

[75] Inventor: Zhou Dehming, Beijing, China

[73] Assignee: Institute of Zoology Academia Sinica, Beijing, China

[21] Appl. No.: 589,726

[22] Filed: Mar. 15, 1984

[51] Int. Cl.⁴ ............................................. G01N 27/28
[52] U.S. Cl. ............................... 204/299 R; 204/182.8
[58] Field of Search ............ 204/299 R, 182.8, 180 G, 204/301

[56] References Cited

U.S. PATENT DOCUMENTS

| | | | |
|---|---|---|---|
| 3,499,833 | 3/1970 | Ferris et al. | 204/299 R |
| 3,657,260 | 4/1972 | McLeester | 204/299 R |
| 3,867,271 | 2/1975 | Hoefer | 204/299 R X |
| 4,048,049 | 9/1977 | Hoefer | 204/299 R |
| 4,101,401 | 7/1978 | Hoefer et al. | 204/299 R X |
| 4,224,134 | 9/1980 | Hoefer et al. | 204/299 R |
| 4,284,491 | 8/1981 | Vesterberg | 204/299 R |

*Primary Examiner*—John F. Niebling
*Assistant Examiner*—B. J. Boggs, Jr.
*Attorney, Agent, or Firm*—Morgan & Finnegan

[57] ABSTRACT

A novel combination vertical gel electrophoresis cell and destainer unit is provided. The cell or destainer comprises two chambers, a first or upper buffer chamber and a second or lower buffer chamber. The upper buffer chamber is a beaker-like container with cooling means, such as a double-wall beaker with an inlet and an outlet for the circulation of a coolant. The lower buffer chamber is a specially designed flask with a shoulder, on which are holes with rubber gaskets for holding the lower ends of gel tubes. The unit further includes a removable electrode for the lower buffer chamber with sufficient water displacement volume to provide hydrostatic equilibrium at the upper and lower ends of the gel tubes. Further, special destaining tubes are provided to convert the electrophoresis cell to a destainer.

23 Claims, 7 Drawing Figures

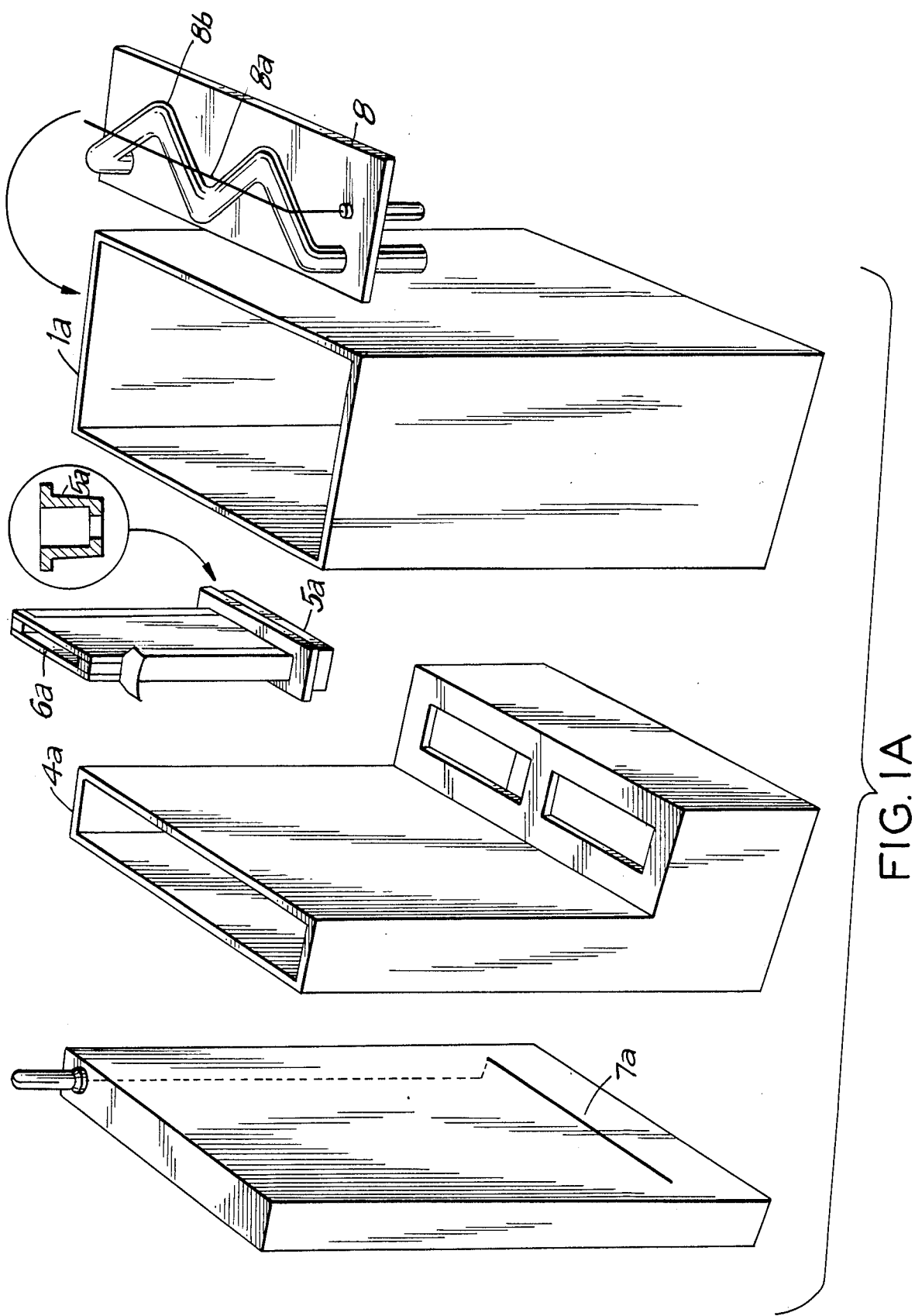

NOVEL GEL ELECTROPHORESIS CELL HAVING A LOWER BUFFER CHAMBER WITH PERFORATED SHOULDER FOR HOLDING GEL TUBES OR CHANNELS

BACKGROUND OF THE INVENTION

The present invention relates to an apparatus suitable for column or slab gel electrophoresis and destaining. More particularly, it relates to a gel electrophoresis cell unit wherein the temperature within a gel medium can be controlled to prevent overheating. This is particularly important for the electrophoresis of biological samples wherein overheating can cause loss in viability.

Gel electrophoresis was explored in the early sixties, by L. Orstein and B. J. Davis using polyacrylamide gels. Since then, the method developed by Orstein and Davis has been applied extensively in the separation of chemical mixtures and identification of their components, particularly for the separation and identification of proteins and nucleic acids in biological fluids.

Vertical gel electrophoresis, one form of gel electrophoresis, is a process for the separation of components in a sample mixture by the application of an electric potential over the length of a gel medium held vertically in a glass tube or channel to cause various components in a sample mixture deposited at one end of a gel medium to differentially migrate over the length of the gel medium. A vertical gel electrophoresis apparatus has mainly two parts: a power supply and an electrophoresis cell unit. The electrophoresis cell unit comprises: a first or upper buffer chamber, a second or lower buffer chamber, an upper electrode, a lower electrode and a plurality of vertically disposed gel columns or slabs having opposite ends opening into the upper and the lower buffer chambers. The upper ends of the gel columns or slabs are in contact with a first or upper buffer solution in the first or upper buffer chamber, and the lower ends of the gel columns or slabs are in contact with a second or lower buffer solution in the second or lower buffer chamber. An electric potential is applied across the ends of the gel columns or slabs by the use of electrodes connected to the power supply and placed separately in the upper and lower buffer solutions.

Until recently, conventional electrophoresis cell units are basically of the same design, employing a holder for gel tubes which also serves as the bottom of the upper buffer chamber. Sealing gaskets on the gel tube holder further serves to separate the buffer solutions in the upper and lower buffer chambers, so that there is no conductance of electricity between the upper and lower buffer solutions except through the gel tubes.

Because of this design, there are several problems. Firstly, the rubber gaskets are inserted into holes on the holder which serves also as the bottom of the upper buffer chamber. This means that the upper buffer chamber must be emptied and inverted for the insertion or extraction of gel tubes. Secondly, the lower ends of all gel tubes held on the holder are immersed in the lower buffer solution simultaneously. This leads to formation of air bubbles at the lower end of the gel tubes. The air bubbles obstruct the flow of electric current through the gel columns, and must be eliminated. However, elimination of all of the air bubbles is troublesome. Thirdly, rubber gaskets, used to hold the gel tubes and to act as seals separating the upper and lower buffer solutions, surround and contact a portion of the gel tubes where the sample gel is usually loaded onto the column. In this portion of the gel tube, the concentration of the sample is relatively high, and is, therefore, more sensitive to heat. The rubber gaskets, being good heat insulators, do not allow a sample in that portion of the tube surrounded by the rubber gasket to be cooled sufficiently. This causes the samples to overheat with concomitant loss of viability, especially in biological samples. Fourthly, the two buffer solutions are usually at different levels which leads to a difference in hydrostatic pressure between upper and lower ends of the gel tubes and also induces an underflow in the gel medium. This disturbs the electrophorectic behavior of the samples, sometimes even causing a low concentration gel to slide out of its supporting glass tube.

In Hoefer, U.S. Pat. No. 3,867,271, an attempt was made to modify the conventional construction of tube gel electrophoresis cell units. The main emphasis was on cooling the gel tubes by inclusion of a central cooling chamber. However both end portions of each gel tube were supported by rubber gaskets. This resulted in less cooling of the gel column than expected. Further, the Hoefer design with its central cooling chamber and provisions for circulating water therein, is complicated, making it hard to manufacture and inconvenient to operate. Moreover, the Hoefer design did not totally overcome the problems in conventional electrophoresis cells units such as: overheating, the formation of air bubbles, or hydrostatic inequilibrium. In fact, two years later, Hoefer, in U.S. Pat. No. 4,048,049, reverted to a more conventional design. The central cooling chamber of his prior design was replaced with a cooling core; the tubes were held in the middle with rubber gaskets. These modifications still did not overcome the problems of bubble formation or hydrostatic inequilibrium and did not completely eliminate the problems of overheating over the entire length of the gel tube. Recently issued U.S. Pat. No. 4,284,491 to Vesterberg, discloses an electrophesis cell unit which is basically the same as Hoefer U.S. Pat. No. 3,867,271 except that the unit has a rectangular rather than a round configuration. Therefore, the various problems discussed above also apply to the Vesterberg design.

Vertical slab gel electrophoresis cells have also followed the conventional design of tube gel electrophoresis cells. As a result, all of the defects described above also applies to vertical slab gel electrophoresis cells. See, for example, U.S. Pat. Nos. 3,932,265; 3,719,580; 4,142,960; 4,290,871; 4,292,161; and 4,224,134.

It is, therefore, an object of the present invention to provide a novel tube gel electrophoresis cell which is simple to manufacture and convenient to operate.

Another object of the invention is to provide an apparatus for vertical gel electrophoresis wherein the gel column will be cooled adequately throughout the migration of the sample on the column to prevent denaturation or loss of viability due to overheating.

A further object of the invention is to provide an apparatus for tube gel electophoresis which is easily convertible to an electrophoresis or diffusion destainer.

SUMMARY OF THE INVENTION

A novel vertical gel electrophoresis cell unit is provided. The novel tube gel electrophoresis cell unit comprises a first or upper buffer chamber and a second or lower buffer chamber. The first or upper buffer chamber is a container surrounded by cooling means. The lower buffer chamber is a flask with a narrow upper part connected via a shoulder plate to a broad lower part, the width or diameter of the lower part being approximately twice the width or diameter of the upper part. On the shoulder plate, holes are provided for the insertion of sealing means having centrally located apertures, for example, toroid gaskets, made of elastomeric material. The gaskets also act as seals to prevent leakage of buffer solutions between the chambers.

The electrophoresis cell unit is assembled for operation as follows. The lower buffer chamber is filled with a buffer solution. The gel tubes or channels are inserted one by one into the gaskets. An electrode is inserted into the lower buffer chamber. This electrode has a large head block with sufficient displacement volume, such that when it is inserted into the lower buffer chamber, the level of the buffer solution in said chamber will rise to a predetermined level. The lower buffer chamber, with the inserted gel tubes or channels and the inserted electrode is placed into a container, preferably a double-walled container with an inlet and an outlet for the circulation of a coolant or a heat exchange medium. Thus, the container functions as the upper buffer chamber and a heat exchanger. Any heat generated in the gel tubes or channels is transmitted out of the container via the upper buffer solution to the heat exchange medium. The upper buffer chamber is filled with buffer solution to a level equal to the level of the buffer solution in the lower buffer chamber. The unit is covered with a lid mounted with an electrode for the upper buffer chamber. The inlet and outlet of the double walled container is connected to a circulating fluid, such as a water faucet. When the electrodes are connected to a power supply, the unit is in operation.

The novel electrophoresis cell unit of the present invention is easy to manufacture, convenient to operate and overcomes all of the above mentioned defects of conventional electrophoresis cell units.

Further, special destaining tubes are provided. The destaining tubes are slightly longer than the gel tubes. The inner diameter of a destaining tube is slightly larger than a gel tube and one end of the destaining tube has been narrowed down to having an inner diameter slightly smaller than that of a gel tube. However, the outer diameter of this end is such that a snug fit is provided when this end is inserted into the gasket. When the gel tubes are replaced with destaining tubes, the same electrophoresis cell functions as a destainer. Moreover, the apparatus of the present invention can be used not only for electrophoresis destaining but also for diffusion destaining.

BRIEF DESCRIPTION OF THE DRAWINGS

FIG. 1A is a construction diagram for the novel electrophoresis cell in a second embodiment.

DETAILED DESCRIPTION OF THE DRAWINGS AND THE PREFERRED EMBODIMENTS

Figure 1:
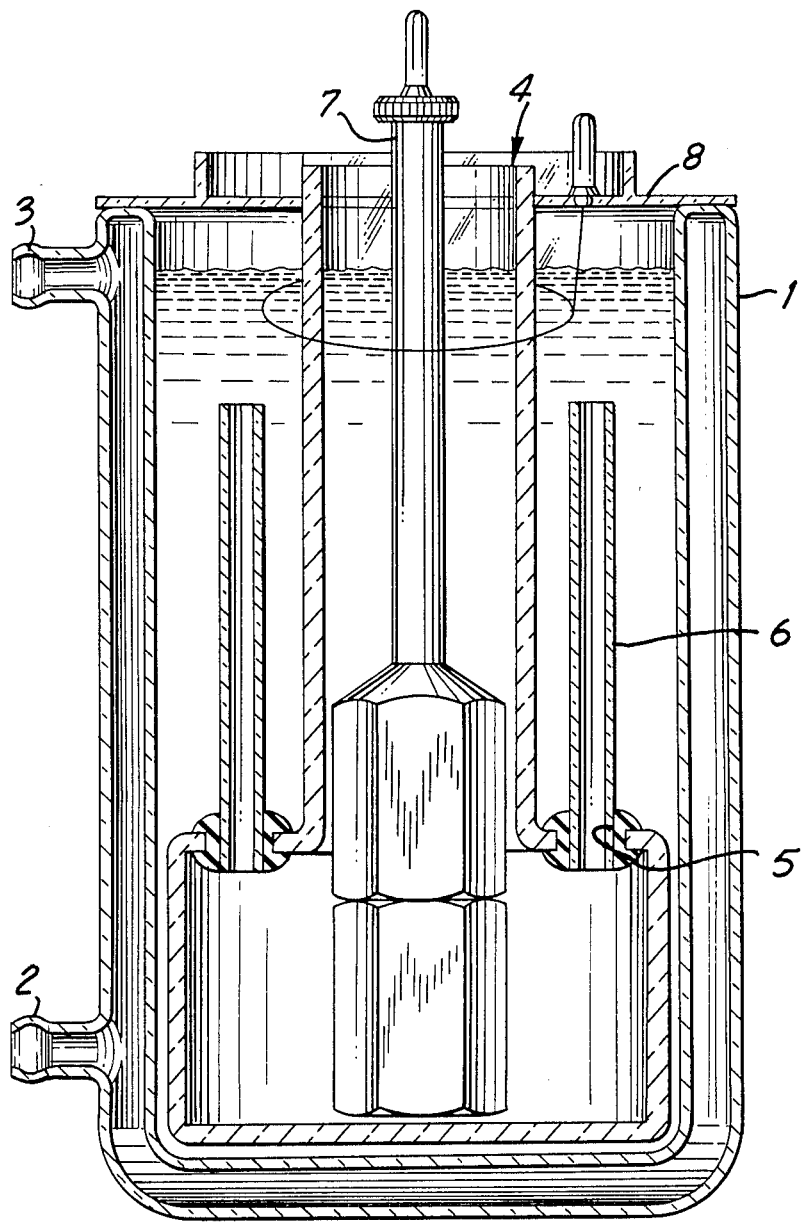
FIG. 1 is a longitudinal cross section of the novel electrophoresis cell ready for electrophoresis.

FIG. 1 shows a longitudinal cross-section of the preferred embodiment of the novel electrophoresis cell unit. A double-walled container (1) with an inlet (2) and an outlet (3) functions both as an upper buffer chamber and a heat exchanger. An inverted T-shaped flask (4) functions as the lower buffer chamber. Holes on the shoulder of the flask are provided with gaskets (5) to hold gel tubes (6). An electrode (7) for the lower buffer chamber comprises an elongated cylindrical upper part and a cylindrical lower part which has a larger diameter than the upper part. The lower part of the electrode thus forms a blockhead with sufficient water displacement volume such that when it is inserted into the lower buffer chamber, the level of the lower buffer solution rises to a predetermined level. A cover (8) is provided to hold the electrode for the upper buffer chamber and to prevent the evaporation of the buffer solutions.

FIG. 1A shows another embodiment of the novel gel electrophoresis unit. The upper buffer chamber (1a) is a tank-like container. Another tank (4a) with a L-shaped cross-section functions as the lower buffer chamber. Channels (6a) and rubber gaskets (5a) are inseted into slots on the shoulder of the lower buffer chamber (4a). Channels (6a) may be made from two pieces of sheet glass, two spacer strips and two pieces of adhesive tape. The rubber gasket (5a) has a protruding collar along the upper edge of the outer wall and an introversive collar flange along the lower edge of the inner wall. The electrode (7a) for the lower buffer chamber is a block with a prefixed water displacement volume and is made of an inert insulating material, preferably, a polymeric material, such as polytetrafluoroethylene, polyacetal, polyvinylchloride, polyamide, and polystyrene. A platinum wire is embedded in the block and held on the surface. One end of the wire is connected to an electric plug on top of the block and the opposite end is placed across the block at approximately the level of the lower ends of the gel tubes. A cover (8) is provided with an electric plug and a platinum wire (8a) connected thereto to form the electrode for the upper buffer chamber and a cooling tube (8b). When the lid is placed on the upper buffer chamber, the upper electrode and the cooling tube are both immersed in the upper buffer solution disposed along the upper ends of the gel channels in the upper buffer chamber.

Figure 2:
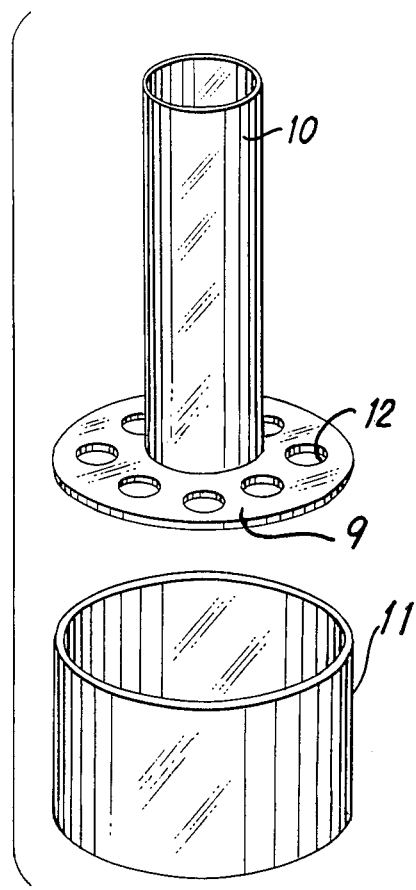
FIG. 2 is a construction diagram for the lower buffer chamber.

FIG. 2 shows how the lower buffer chamber is constructed. A perforated shoulder plate (9), a tube (10) and a broad, cylindrical beaker-like container (11) are combined. The diameter of the container (11) is approximately twice the diameter of the tube (10). Holes (12) are provided on the shoulder plate (9). The lower buffer chamber when assembled is an inverted T-shaped flask with several holes (12) on the shoulder for the insertion of gaskets (5).

Figure 3:
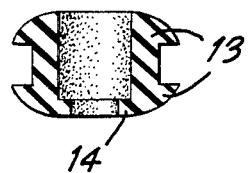
FIG. 3 is a longitudinal cross section of a rubber gasket.

FIG. 3 is the longitudinal cross section of a gasket or sealing means. The gaskets are inserted into holes (12) to hold gel tubes in place during electrophoresis and to prevent leakage of buffer solution between the upper and lower buffer chambers. These should be made of an inert nonpolar elastic material, such as silicon rubber. The gasket is toroid with an upper and lower collar (13) on the outer wall and introversive collar flange (14) along the lower edge of the inner wall. The diameter of the aperture in the gasket is of a size sufficient to provide a snug fit when a gel tube is inserted into the aperture.

Figure 4:
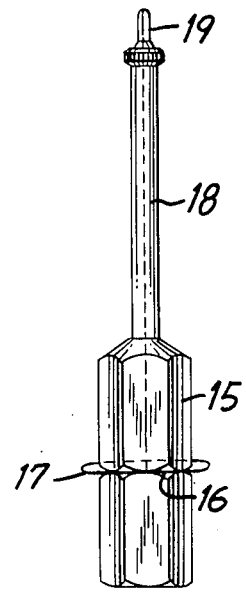
FIG. 4 is a side view of the lower electrode.

FIG. 4 is a side view of the preferred embodiment of the electrode for the lower buffer chamber. The lower part of the electrode is a head block (15) with a prefixed water displacement volume and is made of an inert insulating material, preferably a polymeric material, such as polytetrafluoroethylene, polyacetal, polyvinyl chloride, polyamide, and polystyrene. Around its waist (16) a platinum wire is wound to form a loop-shaped electrode (17) at one end. The radial distance from the platinum wire to the lower end of each gel tube is identical. This ensures that the applied electric potential applied is identical in all of the gel tubes. The opposite end of the platinum wire (17) is passed through a small radial hole in the center of the head block through the elongated tube (18) and connected to an electric plug (19). The nonmetallic part of the electrode supports the platinum wire which is responsible for conduction of electricity.

Figure 5:
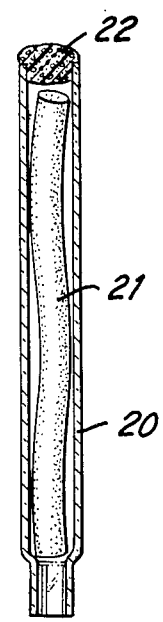
FIG. 5 shows a destaining tube with a gel column ready for destaining.

FIG. 5 shows a destaining tube (20) with a gel column (21) ready for destaining. The destaining tube (20) is made of glass. The inner diameter of the lower end of the tube is slightly smaller than the rest of the tube forming an introversive flange collar, so that one end of the gel column (21) can rest on the flange collar during destaining. The outer diameter of the lower part is of a size sufficient to provide a snug fit when inserted into the aperture of the gasket (5) in FIG. 3. A plug (22) made of polyurethane foam prevents the gel column from floating out of the destaining tube and absorbs dye as it diffuses out of the gel column (21).

Figure 6:
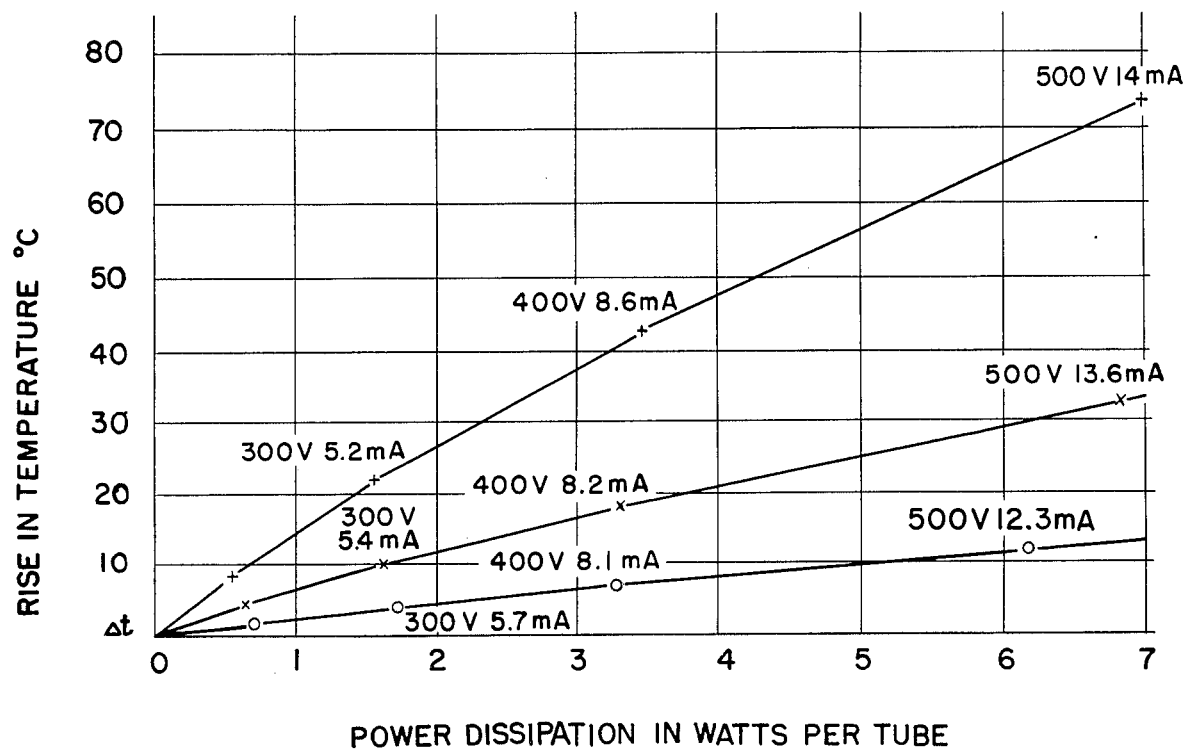
FIG. 6 is a graph showing the temperatures at the center of the gel columns inside gel tubes as measured at various levels of electrical potential.

FIG. 6 is a graph of the increase in temperature at the center point of a test section of a gel column in an assembled tube gel electrophoresis cell unit over the temperature of the external environment. The upper curve represents the increase in temperature inside the gel column when the tube is exposed to air as in conventional electrophoresis cell units without any means of temperature control. The middle curve represents the temperature of a gel column at a point where it is surrounded by a gasket. The bottom curve represents the increase in temperature of a gel column when the test section of the gel tube is directly immersed in a liquid medium.

The upper buffer chamber is a beaker-like or tank-like container made from inert transparent materials, preferably glass. The beaker or tank may be double-walled with an inlet and an outlet as shown in FIG. 1, or the beaker or tank may be encircled with cooling means, such as, a water bath or a water jacket. The double-walled beaker or tank with cooling means serves as a heat exchanger in addition to being the upper buffer chamber. Moreover, in the apparatus of the present invention, the upper buffer solution serves as a heat-conducting medium to transmit heat generated in gel tubes to the external environment. Thus, it is preferable that a large surface area of the heat-exchange medium is in contact with a large surface area of the container for the upper buffer solution to provide the best temperature control.

The electrode for the upper buffer chamber is a platinum wire. The platinum wire may be shaped into a ring at one end. The ring diameter is slightly larger than the upper part of the lower buffer chamber, and is hung under the center of the cell lid. The platinum wire may also be a straight piece of wire held under the lid. The other end of the platinum wire electrode is connected to an electric plug set on the cell lid. During electrophoresis, the cell is covered with the cell lid and the electrode for the upper buffer chamber will be properly positioned around or along the top of the elongated upper part of the lower buffer chamber and immersed in the upper buffer solution.

In operation, the lower buffer chamber is filled with a buffer solution to a level slightly higher than the upper edge of the gaskets. The gaskets are made of a nonpolar hydrophobic material. As a result, a convex liquid bubble forms at each gasket due to the high hydrostatic pressure and surface tension. Gel tubes or channels then are inserted in turn into the holes of the gasket. Because of the introversive collar flange on the inner wall of the gasket, the tip of each gel tube or channel butts against the collar flange and the gel tube or channel is prevented from being inserted too far into the gasket. In this manner, no air bubbles will form at the lower end of the gel tubes or channels. It is not necessary to invert the buffer chamber for the insertion or removal of gel tubes or channels and there is no leakage of buffer solutions out of the buffer chamber. This provides a convenient means for loading the electrophoresis cell, and overcomes the problems associated with loading the gel tubes or channels in the electrophoresis cells of the prior art.

The electrode for the lower buffer chamber then is lowered into the lower buffer chamber. The level of buffer solution in the lower buffer chamber will rise to a level determined by the displacement volume of the electrode.

The lower buffer chamber with the gel tubes or channels is placed into the upper buffer chamber. The upper buffer chamber is filled with a volume of upper buffer solution to a level identical to that of the buffer solution in the lower buffer chamber to provide hydrostatic equilibrium at both ends of the gel tubes or channels. The cell is covered with the cell lid. The inlet and outlet of the water jacket or double-walled beaker or tank is connected to a cold water faucet; or, if no water jacket or double wall is provided, the beaker or tank is placed into a constant temperature bath. The electrodes then are connected to a power supply for electrophoresis.

On completion of electrophoresis, the procedure is reversed. The process steps may be modified as long as the spirit of the invention is observed.

The design of the apparatus of the present invention avoids the formation of air bubbles at the lower ends of the gel tubes or channels and provides excellent means for cooling the gel columns or slabs during electrophoresis. Each of the gaskets are designed with an introversive collar flange along the lower edge of the inner wall of the gasket so that the lower tip of the gel tube or channel butt against the introversive collar flange and is held only at this point by the gasket. Generally, if the electrophoresis is carried out properly, none of the components to be separated will reach the lower tip of the gel tube or channel. Therefore, this design in combination with the large heat exchange surface provided by the double-walled beaker, ensures sufficient cooling of the gel tubes or channels and the samples therein, so that little or no damage to the sample caused by overheating will be observed. In contrast, in the conventional electrophoresis cell unit, little or no cooling is provided. Each gel tube has a section exposed to air, a section immersed in buffer solution and a section surrounded by a rubber gasket.

A simulated test was designed to measure the cooling efficiency by burying a thermocouple at the center of the test section of a gel column in an electrophoresis cell unit. The following measurements were taken using a conventional electrophoresis cell unit.

Gel tubes with an external diameter of 7 mm and an internal diameter of 5 mm and a length of approximately 8 cm were used. The tubes were filled with 7.5% polybutylacrylamide gel. The buffer solution in both upper and lower buffer chambers and in the gel is 0.02M tris-hydroxymethylaminomethaneborate-EDTA buffer of pH 8.3. The electrical conductivity of the solution is 0.00088 ohm$^{-1}$.

A conventional electrophoresis cell unit was assembled. The temperatures ($T_1$) at the center of the gel columns and, the temperature ($T_2$) of the surroundings outside the electrophoresis gel tube were measured simultaneously. The results are shown in FIG. 6. The upper curve represents the difference in temperature ($T_1 - T_2$) when a gel tube is exposed to air. The middle curve represents the difference in temperature ($T_1 - T_2$) when a tube is surrounded by a rubber gasket and immersed in a buffer solution. The lower curve represents the situation when the gel tube is surrounded with buffer solution. For example, if the surrounding temperature is about 5° C. and if the power dissipation is about 5 watts per tube, the components to be separated will suffer a temperature increase of about 62° C. in a conventional unit, of about 30° C. in a cell unit according to Hoefer U.S. Pat. No. 4,048,049, and of about 15° C. in a cell unit according to the present invention. This is because in a conventional unit, every gel tube has a section exposed to air; and in a cell unit according to Hoefer U.S. Pat. No. 4,048,049, the middle sections of the gel tubes are surrounded by rubber gaskets. Whereas, in a cell unit according to the present invention, no part of the gel tube is exposed to air, and only the bottom end of the gel tubes, not reached by any component, are surrounded by rubber gaskets.

Furthermore, the apparatus of the present invention can be easily modified into a destaining unit. Special destaining tubes are provided.

The destaining tubes are modified gel tubes with a slightly larger inner diameter. One end of the tube is modified to have a slightly smaller diameter than the inner diameter of the rest of the tube to form an introversive collar. However, the outer diameter of this end is equal to that of a standard gel tube. When a gel column is inserted into a destaining tube, one end will rest on the collar. A porous plug made preferably from polyurethane foam is provided for the top end to absorb any dye diffusing out of the gel column.

When the gel tubes are replaced with the special destaining tubes and the buffer solution is replaced with destaining solution, the apparatus of the present invention becomes a destainer, and may be used either for electrophoresis destaining or diffusion destaining. For electrophoresis destaining, the same power supply used for electrophoresis may be employed; it no longer is necessary to employ another special lower voltage high current power supply. In diffusion destaining, the power supply and the electrodes may be omitted. In place of the power supply, a small pump is used to continuously pump the destaining solution from the upper buffer chamber to the lower buffer chamber. The difference in liquid levels between the chambers causes an upward flow of the destaining solution out of the lower buffer chamber around each gel column and carries away dye diffusing out of the gel column. The dye then is absorbed by the polyurethane foam plug placed at the top end of the gel tube.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

I claim:

1. A gel electrophoresis cell unit, comprising:
   (a) an upper buffer chamber, containing an upper buffer solution, in the form of a first container having an open end and surrounded with cooling means;
   (b) a lower buffer chamber, containing a lower buffer solution in the form of a second container with a shoulder and a plurality of holes in the shoulder, the lower buffer chamber being removably immersed in the upper buffer solution in the upper buffer chamber;
   (c) a plurality of toroid sealing means having centrally located apertures removably inserted into said plurality of holes;
   (d) a plurality of gel holders with upper and lower ends each containing a gel medium for electrophoresis, the lower ends of the gel holders being removably inserted into the apertures of the toroid sealing means;
   (e) an electrode for said lower buffer chamber inserted into the lower buffer chamber;
   (f) an electrode for the upper buffer chamber inserted into the upper buffer chamber; and
   (g) covering means removably mounted over the upper and lower buffer chambers.

2. A gel electrophoreses unit according to claim 1 wherein each gel holder is in the form of a tube.

3. A gel electrophoresis unit according to claim 1 wherein each gel holder is in the form of a channel.

4. A gel electrophoresis unit according to claim 1 wherein said upper buffer chamber is a double-walled beaker with an inlet and outlet on the external wall of the double-walled beaker.

5. A gel electrophoresis unit according to claim 1 wherein the lower buffer chamber is a flask with a cross-section in the shape of an inverted T.

6. A gel electrophoresis unit according to claim 1 wherein each of said toroid sealing means are provided with an introversive collar flange along the lower edge of the inner wall of said toroid sealing means.

7. A gel electrophoresis unit according to claim 6 wherein the non-metallic part of the electrode for said lower buffer chamber is made of a material selected from the group consisting of polytetrafluoroethylene, polyacetal, polyvinyl chloride, polyamide, and polystyrene.

8. A gel electrophoresis unit according to claim 1 wherein the toroid sealing means are made of non polar elastomeric material.

9. A gel electrophoresis unit according to claim 1 wherein the toroid sealing means are made of silicone rubber.

10. A gel electrophoresis unit according to claim 1 wherein the electrode for said lower buffer chamber comprises: a non-metallic part, comprising an elongated tube with a block head with sufficient water-displacement volume to adjust the buffer solution level of said lower buffer chamber to a predetermined level; and a metallic part, comprising a platinum wire for the conductance of electricity mounted in said elongated tube, with a first end of said platinum wire connected to an electric plug mounted on top of said elongated tube and with a second end of said platinum wire in the shape of a ring mounted on the exterior toward the center of said block head.

11. A gel electrophoresis unit according to claim 1 wherein said electrode for the upper buffer chamber is a platinum wire with one end connected to an electric plug mounted on said covering means, and the other end in the shape of a ring hanging below the center of said covering means.

12. An electrorphoresis destaining cell unit comprising:
   (a) an upper buffer chamber with destaining solution in the form of a first container having an open end and surrounded with cooling means;
   (b) a lower buffer chamber with destaining solution in the form of a second container with a shoulder and a plurality of holes on said shoulder, removably immersed in the buffer solution in the upper destaining chamber;
   (c) a plurality of toroid sealing means having centrally located apertures removably inserted into said plurality of holes on said shoulder of said second container;
   (d) a plurality of destaining tubes with upper and lower ends for holding gel columns for destaining and with the lower end of each destaining tube removably inserted into said toroid sealing means;
   (e) an electrode for the lower buffer chamber inserted into the lower buffer chamber;
   (f) an electrode for the upper buffer chamber inserted into the first container; and
   (g) covering means removably mounted over the upper and lower buffer chambers.

13. An electrophoresis destaining cell unit according to claim 12 wherein said upper buffer chamber is a double-walled beaker with an inlet and outlet on the external wall of the double-walled beaker.

14. An electrophoresis destaining cell unit according to claim 12 wherein said lower chamber is a flask with a cross-section in the form of an inverted T.

15. An electrophoresis destaining cell unit according to claim 12 wherein each of the toroid sealing means are provided with an introversive collar flange along the lower edge of the inner wall of the toroid sealing means.

16. An electrophoresis destaining cell unit according to claim 12 wherein the toroid sealing means are made of non-polar elastomeric material.

17. An electrophoresis destaining cell unit according to claim 16 wherein the non-metallic part of the electrode for the lower buffer chamber is made of a material selected from the group consisting of polytetrafluoroethylene, polyacetal, polyvinyl chloride, polyamide, and polystyrene.

18. An electrophoresis destaining cell unit according to claim 17 wherein the destaining tube is further provided with a porous plug for the upper end of the destaining tube.

19. An electrophoresis destaining cell unit according to claim 18 wherein the porous plug is made of polyurethane foam.

20. An electrophoresis destaining cell unit according to claim 12 wherein the toroid sealing means are made of silicone rubber.

21. An electrophoresis destaining cell unit according to claim 12 wherein the electrode for the lower buffer chamber comprises a non-metallic part, comprising an elongated tube with a block head of sufficient water-displacement volume to adjust the buffer solution level of said lower buffer chamber to a predetermined level; and a metallic part, comprising a platinum wire for the conductance of electricity mounted in said elongated tube, with a first end of said platinum wire connected to an electric plug mounted on top of said elongated tube and with a second end of said platinum wire in the shape of a ring mounted on the exterior toward the center of said block head.

22. An electrophoresis destaining cell unit according to claim 12 wherein the electrode for the upper buffer chamber is a platinum wire with one end connected to an electric plug mounted on said covering means and the other end in the shape of a ring hanging below the center of said covering means.

23. An electrophoresis destaining cell unit according to claim 12 wherein the lower end of each destaining tube is provided with an inner diameter slightly smaller than the inner diameter of the remaining length of said destaining tube.

* * * * *

UNITED STATES PATENT AND TRADEMARK OFFICE
CERTIFICATE OF CORRECTION

PATENT NO. : 4,613,419
DATED : September 23, 1986
INVENTOR(S) : ZHOU, Dehming

It is certified that error appears in the above-identified patent and that said Letters Patent is hereby corrected as shown below:

In the heading, delete "Dehming" and insert therefore --ZHOU--.

In Claim 12, line 1, delete "electrorphoresis" and insert therefor --electrophoresis--.

Signed and Sealed this

Twenty-third Day of December, 1986

Attest:

DONALD J. QUIGG

*Attesting Officer*  *Commissioner of Patents and Trademarks*